United States Patent [19]

Lin et al.

[11] 4,446,065

[45] May 1, 1984

[54] PHENCYCLIDINE COMPOUNDS AND ASSAYS FOR ITS DETERMINATION

[75] Inventors: Cheng-I Lin, San Jose; Prithipal Singh, Sunnyvale, both of Calif.

[73] Assignee: Syva Company, Palo Alto, Calif.

[21] Appl. No.: 333,344

[22] Filed: Dec. 22, 1981

[51] Int. Cl.$^3$ .................. C12N 9/96; G01N 33/54; A61K 43/00

[52] U.S. Cl. ................ 260/112 R; 260/112 B; 260/121; 260/172; 435/7; 435/188; 424/85

[58] Field of Search .............. 260/112 R, 112 B, 121, 260/172; 435/7, 188; 424/85

[56] References Cited

U.S. PATENT DOCUMENTS 4,196,185 4/1980 Focella et al. .................. 424/1
4,281,065 7/1981 Lin et al. .................. 435/188

*Primary Examiner*—John Kight, III
*Assistant Examiner*—Nathan M. Nutter
*Attorney, Agent, or Firm*—Bertram I. Rowland

[57] ABSTRACT

Novel oxime derivatives of phencyclidine are provided as precursors for conjugating proteins, either antigenic for the preparation of antibodies or enzymatic for the preparation of enzyme conjugates, which antibodies and enzyme conjugates find use as reagents in immunoassays. The combination of antibodies and enzyme conjugates provide for sensitive, accurate, rapid assays for phencyclidine without interference from commonly administered drugs, such as dextromethorphan, demerol and chlorpromazine.

9 Claims, No Drawings which are capable of clinically distinguishing PCP from structurally similar compounds, such as dextromethorphan, demerol and chlorpromazine.

The antigen compounds may be injected into a wide variety of vertebrates in accordance with conventional methods for the production of antibodies. Usually the animals are bled periodically with successive bleeds having improved titer and specificity, until reaching a plateau and then diminishing in their specificity and titer. The antigens may be injected intramuscularly, intraperitoneally, subcutaneously, or the like. Usually a vehicle is employed, such as complete or incomplete Freund's adjuvant.

The antibodies and enzyme reagents prepared in accordance with the subject invention find particular use in immunoassays for the determination of PCP in biological specimens. A description of the method for carrying out a homogeneous enzyme immunoassay may be found in U.S. Pat. No. 3,817,837. The method involves combining the enzyme conjugate, the unknown sample suspected of containing PCP, and an antibody for PCP in an aqueous buffered medium at temperatures in the range from about 10°–50° C., usually from about 20°–40° C.

Both the antibodies and enzyme reagents of the present invention may be employed in assays where the corresponding reagent is obtained from a precursor other than the oximes herein described. For example, antibodies prepared from PCP oxime conjugates may be employed with another PCP derivative conjugated to an enzyme label, e.g., PCP acid conjugated to G6PDH as set forth in the Examples.

The following examples are offered by way of illustration and not by way of limitation.

EXPERIMENTAL

All temperatures not otherwise indicated are in centigrade. All parts and percentages are by weight, except for mixtures of liquids which are by volume. The following abreviations are used: THF—tetrahydrofuran; DCC—dicyclohexyl carbodiimide; G6PDH—glucose-6-phosphate dehydrogenase; NHS—N-hydroxy succinimide; DMF—dimethylformamide; BSA—bovine serum albumin; BgG—bovine gamma-globulin; HOAc—glacial acetic acid; EDCI—ethyl dimethylaminopropyl carbodiimide.

EXAMPLE I

Preparation of O-Carboxymethyl Oxime of 4-Phenyl-4-piperidinocyclohexananone (PCP Oxime)

A. Preparation of Quinitol Monobenzoate

Quinitol (17 g, 0.146 mole) was dissolved in 300 ml of dry chloroform and 120 ml of pyridine (0.15 mole) was added to it. The solution was cooled with an external ice-bath and was slowly added to a solution of 19.6 g of benzoyl chloride (0.14 mole) in 60 ml of chloroform with vigorous stirring. After completion, the mixture was stirred at room temperature overnight. The solution was then washed with 3×100 ml of water. The organic solution was dried over sodium sulfate and was concentrated to give an oil residue. The residue was fractionated to give 19.7 g of the desired monobenzoate as a colorless very viscous oil (bp: 143° C./0.01 mm Hg) in 61% yield.

B. Preparation of 4-Benzoyloxycyclohexanone

Chromium trioxide (8 g), dissolved in 10 ml of water and 20 ml of glacial acetic acid, was slowly added to a stirred and cooled solution of quinitol monobenzoate (18 g, 0.08 mole) in 35 ml of glacial acetic acid. The temperature was kept below 35° C. After completion, the mixture was allowed to stir at room temperature overnight. Water was added to it and the mixture was extracted with 5×150 ml of ethyl ether. The ethereal solution was washed with 3×100 ml of water, 2×100 ml of dilute sodium hydroxide solution, and then was dried over sodium sulfate and was concentrated under reduced pressure to give a white solid residue. Recrystallization from petroleum ether:hexane (50:50 v/v) gave 14.5 g of white crystalline solid (mp: 62°–3° C.) in 83% yield.

C. Preparation of 4-Benzoyloxy-1-piperidinocyclohexanecarbonitrile

4-Benzoyloxycyclohexanone (13.5 g, 62 mmoles), piperidine hydrochloride (8.1 g, 67 mmoles) and potassium cyanide (4.25 g, 65 mmoles) were dissolved in 60 ml of 95% ethanol and 60 ml of water. The mixture was stirred at room temperature for 16 hours (overnight). The resulting solid material was collected by filtration. The filtrate was diluted with 100 ml of water and the solution was extracted with ether. Concentration of the ethereal solution gave more solid material. The combined solid material was recrystallized from 90% ethanol to give 14.5 g of white crystalline solid (mp: 165°–171° C.) in 75% yield.

D. Preparation of 4-Phenyl-4-piperidinocyclohexanol

4-Benzoyloxy-1-piperidinocyclohexylcarbonitrile (7.7 g, 25 mmoles) was dissolved in 150 ml of anhydrous THF under argon. Phenylmagnesium bromide (3 M in ether, 50 ml, 150 mmoles) was slowly added via a hypodermic syringe with vigorous stirring. After completion of the reaction, the mixture was stirred at approximately 55° C. for 3 hours and then at room temperature overnight. Saturated ammonium chloride solution was carefully added and the mixture was extracted with ethyl ether. The combined organic solutions were concentrated under reduced pressure and the residue was taken up with 300 ml of ethyl ether. The ethereal solution was extracted with 3×100 ml of 6 N HCl. The aqueous solution was carefully made basic with ammonium hydroxide. The white precipitate was collected by filtration. Recrystallization from hexane (with a small amount of ethanol) gave 2.7 g of a white crystalline solid (mp: 162°–5° C.) in 40% yield. TLC analysis indicated it was a mixture of two isomers.

E. Preparation of 4-Phenyl-4-piperidinocyclohexanone

4-Phenyl-4-piperidinocyclohexanol (1.2 g, 4.6 mmoles) was dissolved in 50 ml of glacial acetic acid. The solution was cooled with an external ice-bath. Chromium trioxide (1 g, 10 mmole) was dissolved in 10 ml of water and 15 ml of glacial acetic acid, and was slowly added to the solution. After completion, the solution was stirred at room temperature for 4 hours. TLC analysis indicated no starting material was left. The solution was cooled with an ice-bath and was carefully made basic with sodium hydroxide solution. The greenish solution was extracted with 5×60 ml of ethyl ether. The combined ethereal solutions were dried over sodium sulfate and were concentrated under reduced pressure to give a white solid residue. Recrystallization from hexane gave 1.1 g of slightly brown crystalline solid (mp: 116°–117° C.) in 93% yield.

PHENCYCLIDINE COMPOUNDS AND ASSAYS FOR ITS DETERMINATION

BACKGROUND OF THE INVENTION

1. Field of the Invention

Phencyclidine is an hallucinogenic drug and it is desirable to be able to rapidly and reliably determine its presence in sera, even at low concentrations. In preparing an immunoassay for phencyclidine, it is desirable to prevent cross-reactivity with other drugs, such as dextromethorphan, demerol, and chlorpromazine which may be present and have clinically similar symptoms. Such cross-reactivity can lead to false indications that the drug is present in a particular sample. To this purpose it is necessary to devise immunogenic conjugates of the phencyclidine hapten to elicit antibodies which provide the desired degree of clinical specificity, while having high binding affinities and titer.

2. Description of the Prior Art

See, Lin, et al., *Biomedical Mass Spectrometry*, 1975, 2:206.

SUMMARY OF THE INVENTION

Oxime derivatives of phencyclidine are provided as precursors for conjugating to proteins, such as antigens and enzymes. The antigens are used for production of antibodies to phencyclidine, which antibodies together with the enzyme conjugates are used as reagents in sensitive immunoassays for monitoring phencyclidine in serum. Both the antibodies and the enzyme conjugates may be used in assays where the corresponding reagent is derived from other than an oxime derivative of phencyclidine.

DESCRIPTION OF THE SPECIFIC EMBODIMENT

Oxime derivatives of phencyclidine (PCP) are provided as precursors to protein conjugates where the proteins are antigens or enzymes. The antigenic conjugates are employed for the production of antibodies which are used in conjunction with the enzyme conjugates in sensitive immunoassays for PCP.

The compounds of the subject invention will have the following formula:

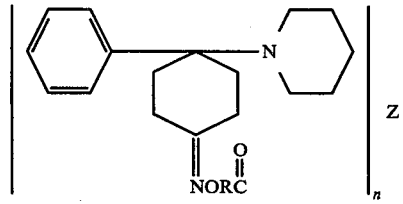

wherein:
R is an aliphatic linking group having at least one carbon atom and not more than about six carbon atoms; usually one to four carbon atoms, which are saturated aliphatic, for example, R may be methylene, ethylene, propylene and 2-methylethylene;

Z is hydrogen, hydroxyl, alkoxyl having from one to six carbon atoms, a group forming an activated ester capable of amide formation in an aqueous medium, or a poly(amino acid) which is antigenic or an enzyme;

n is one when Z is other than a poly(amino acid) and is otherwise in the range from one to the molecular weight of Z divided by 500, more usually divided by 1,000 and frequently divided by 1,500;

when Z is an antigen, n usually ranges from one to 500, typically from 10 to 100; and when Z is an enzyme, from one to 30, more usually two to 20, and preferably from two to 16.

The poly(amino acids) will generally range from about 5,000 molecular weight, having no upper molecular weight limit, normally being less than 10,000,000, and usually being not more than about 600,000. There will usually be different ranges depending on whether an antigen or an enzyme is involved. With antigens, the range will be from about 5,000 to 10,000,000, usually from about 20,000 to 600,000, and more usually from about 25,000 to 250,000 molecular weight. With enzymes, the range will be from about 10,000 to 600,000, and more usually from about 10,000 to 300,000 molecular weight. For both antigens and enzymes, there will usually be at least about 1 PCP group per 500,000 molecular weight, more usually at least one per 50,000 molecular weight. In the case of intermediate molecular weight antigens (35,000 to 600,000), the number of PCP groups will generally be from about 2 to 250, more usually from 10 to 100. With lower molecular weight antigens, (below 35,000), the number of PCP groups will generally be in the range from about 2 to 10, usually in the range from 2 to 5.

Various protein types may be employed as the antigenic material. These types include albumins, serum proteins, e.g., globulins, ocular lens proteins, lipoproteins, and the like. Illustrative proteins include bovine serum albumin, keyhole limpet hemocyanin, egg ovalbumin, bovine gamma-globulin, and the like. Alternatively, synthetic poly(amino acids) may be prepared having sufficient available amino groups, e.g., lysines.

The enzymes can vary widely, depending on the ease of conjugation, turnover rate, and the physiological fluid in which the phencyclidine is to be measured. Primarily, the enzymes of choice, based on the I.U.B. classifications are: Class 1, Oxidoreductases and Class 3, hydrolases. Particularly in Class 1, the enzymes of interest are dehydrogenases of Class 1.1, more particularly, Sub-classes 1.1.1 and 1.1.99 and peroxidases in Class 1.11. Of the hydrolases, particularly Class 3.1, more particularly 3.1.3 and Class 3.2, more particularly 3.2.1.

Illustrative dehydrogenases include malate dehydrogenase, glucose-6-phosphate dehydrogenase, and lactate dehydrogenase. Illustrative peroxidases include horseradish peroxidase, and illustrative hydrolases include alkaline phosphates, beta-galactosidase, beta-glucosidase and lysozyme.

Particularly preferred are those enzymes which employ nicotinamide adenine dinucleotide (NAD), or its phosphate (NADP) as a cofactor, particularly the former, or the reduced forms thereof. Illustrative of these enzymes is glucose-6-phosphate dehydrogenase.

The subject precursors can be prepared from commercially available materials, such as 1,4-cyclohexanediol, piperidine and phenylmagnesium bromide, as described in the Examples hereinafter.

By employing the procedure to be exemplified, PCP is functionalized to a compound which can be readily conjugated to poly(amino acids), either antigenic or enzyme. The structure of the PCP is retained during the synthesis and those elements of the structure which provide for distinction between closely similar compounds are exposed to allow for formation of antibodies

F. Preparation of O-Carboxymethyl oxime of 4-phenyl-4-piperidinocyclohexanone 4-Phenyl-4-(1-piperidino)cyclohexanone (0.95 g, 3.7 mmoles) and sodium acetate (0.5 g, 61 mmoles) were dissolved in 40 ml of isopropanol and 10 ml of water. Aminooxyacetic acid hydrochloride (0.5 g) in 10 ml of water was added to the aqueous isopropanolic solution at room temperature. The solution was allowed to stir for 1 hour at room temperature. Solvent was removed under reduced pressure and the residue was extracted with chloroform. The organic solution was concentrated and the residue was chromatographed on silica gel plates with $CH_3OH:CHCl_3:NH_3$ (4:6:1) (saturated with anhydrous $NH_3$) as eluant to give 1.2 g of the desired product as a solid (mp: 172°-5° C.) in 96% yield ($R_f$ 0.27).

EXAMPLE II

Conjugation of PCP Oxime to BSA and BgG

The O-carboxymethyl oxime of 4-phenyl-4-piperidino-cyclohexane (Example I) (150 mg, $4.54 \times 10^{-4}$ mole), NHS (63 mg, $5.5 \times 10^{-4}$ mole) and DCC (103 mmole, $5.5 \times 10^{-4}$ mole) were placed in a 5 ml flask. The flask was connected to a vacuum line for 30 minutes. DMF (2 ml, dried over molecular sieves) was added to the mixture and the resulting mixture was stirred at ice-bath temperature for 2 hours and then allowed to stir in the cold room overnight yielding an activated NHS-ester.

BSA (Miles Lab. Lot #35, 500 mg) was dissolved in 40 ml of $NaHCO_3-Na_2CO_3$(0.1 N) buffer solution and the solution was cooled in an ice-bath. The activated NHS-ester was slowly added to the cold BSA solution by filtering through a glass-wool packed pipet with stirring. After completion, the solution was stirred in the cold room overnight before dialysis.

The same procedure was used for BgG conjugation (Miles Lab., Lot #1074, 530 mg in 80 ml of buffer).

Dialysis and purification were performed conventionally. Hapten number was determined by the TNBS method (Habeeb, Anal. Biochem. 14, 328 (1966)) to give 15 for BSA-conjugation and 30 for BgG-conjugation.

EXAMPLE III

Conjugation of PCP Oxime to G6PDH

The O-carboxymethyl oxime of 4-phenyl-4-piperidino-cyclohexanone (Example I) (33 mg, 0.1 mmole) dried at 60° C. under vacuum for 16 hours, dry NHS (12.65 mg, 0.11 mmole) and dry EDCI (21.12 mg, 0.11 mmole) were placed in a dried pear-shaped flask (5 ml) with a side arm. The flask was equipped with a stirring bar, serum stopper and drying tube. DMF (2 ml, dried over 4 A sieves) was added to the flask and the mixture stirred for 16 hours at room temperature to form the activated ester.

G6PDH (2 ml, 2.51 mg/ml), NADH (60 mg) and G6P-disodium salt were placed in a flask equipped with a stirring bar. The mixture was stirred to effect solution and cooled in an ice-water bath (4° C.). Activated ester was added in increments of 2 ml using a syringe to an end point of 40 μl over a period of 30 minutes. The addition of activated ester was terminated at an end point of 55.7% maximum inhibition and a deactivation of 16.5% of the enzyme activity. The crude enzyme conjugate was chromatographed through a Sephadex ® G-50 column.

EXAMPLE IV

Preparation of PCP Acid and Activated Ester of PCP Acid

A. Preparation of 1-Piperidinocyclohexanecarbonitrile

Piperidine (44 g, 0.52 mole) was carefully mixed with 45 ml of concentrated HCl and 120 ml of cold water (pH 3-4). To this solution, 50 g (0.52 mole) of cyclohexanone was added, followed by 36 g of KCN in 100 ml of water with vigorous stirring. The resulting solution was allowed to stir at room temperature for overnight. After 2 hours, a white precipitate was formed. The crystalline precipitate was collected by filtration and washed with cold water. Recrystallization from 95% ethanol (300 ml) gave 88 g of white crystalline solid, mp 66°-8° C., in 88% yield.

B. Preparation of Tetrahydropyran (THP) Protected p-Bromophenethyl Alcohol p-Bromophenethyl alcohol (Aldrich, 10.5 g, 0.05 mole) was added to a stirring solution of 10 g (0.12 mole) dihydropyran in 100 ml of ethyl ether containing a few crystals of p-tolylsulfonic acid. The solution was stirred at room temperature for one hour and then was added 10 ml of 0.1 N sodium hydroxide. The aqueous solution was separated and the ethereal solution was dried over sodium sulfate. Concentration and vacuum distillation, bp. 134°-5° C./0.5 mm, afforded 12.4 g of clear liquid as the desired product in 87% yield.

C. Preparation of 1-(1-Phenylcychexyl)piperidine Alcohol Derivative (PCP-Alcohol Derivative)

Tetrahydropyran protected p-bromophenethyl alcohol (8 g, 0.028 mole) was dissolved in 150 ml of freshly distilled anhydrous THF in a 500 ml flask under argon. To this solution, magnesium (1.2 g, washed with dil. HCl, acetone, ether and dried) was added, followed by a few pieces of iodine and a few drops of dibromoethane. As soon as there was gas evolution, the solution was heated to approximately 60° C. with stirring. The mixture was stirred at 60° C. for 4 hours under argon. After cooling to room temperature, a solution of 5.4 g (0.028 mole) 1-piperidinecyclohexanecarbonitrile in 50 ml of anhydrous THF was slowly added with vigorous stirring. After completing the addition, the solution was allowed to stir at room temperature overnight. Saturated ammonium chloride (50 ml) was added followed by 200 ml of ethyl ether. The organic solution was separated and was dried over sodium sulfate. Solvent was removed under reduced pressure to give a brown liquid. The crude product was dissolved in 200 ml of ether and was extracted with $3 \times 60$ ml of 20% HCl solution. The combined aqueous solution was extracted with $2 \times 100$ ml of ethyl ether. The aqueous solution was then adjusted to approximately pH 8 with ammonium hydroxide and was extracted with $5 \times 100$ ml of ethyl ether. The ethereal solution was dried over sodium sulfate and was concentrated under reduced pressure to give 6.5 g of desired product as heavy oil in 88% yield.

D. Preparation of Ester of PCP-alcohol Derivative (PCP-ester)

A solution of PCP-alcohol derivative (6.1 g, 0.021 mole) in 35 ml of anhydrous DMF (distilled over $CaH_2$) was added to a suspended sodium hydride (50% oil dispersion, 1.44 g, 0.03 mole, washed with $3 \times 10$ ml of petroleum ether) solution (60 ml of anhydrous DMF) under argon atmosphere. The solution was heated at approximately 55° C. for 2 hours and then cooled to room temperature. Ethyl bromoacetate (5 g, 0.03 mole) in 40 ml of DMF was then dropwise added. After complete addition, the solution was allowed to stir at room temperature overnight. After a small amount of water was added, the solution was concentrated to dryness under vacuum. The residue was taken up with chloroform. The chloroform solution was chromatographed on silica gel thin layer plates (20% methanol/chloroform) to give three major components:

Fraction 1, $R_f$ 0.04, was collected in 0.85 g and was identified as styrene derivative, in 15% yield.

Fraction 2, $R_f$ 0.89, was collected in 1.45 g as the desired ester, in 18.5% yield.

Fraction 3, $R_f$ 0.4, was identified as starting material (2.4 g).

E. Hydrolysis of PCP-Ester to Form PCP-Acid

PCP-ester (1.43 g, $3.8 \times 10^{-3}$ mole) was dissolved in 40 ml of methanol and was added 10 ml of 1 N sodium hydroxide solution was then added. The mixture was allowed to stir at room temperature for 4 hours. The solution was concentrated to dryness under vacuum and the residue was dissolved in 20 ml of water. The aqueous solution was adjusted to approximately pH 6 by treatment with acetic acid. The solution was then concentrated to dryness under vacuum. The solid residue was extracted with chloroform several times. The combined organic solution was concentrated and the residue was chromatographed on silica gel plate with a 20% methanol-chloroform solution (saturated with anhydrous ammonia) as eluent ($R_f$ 0.3) to give 1.1 g of the corresponding acids, in 83% yield, mp: 198°–200° C.

F. Preparation of Activated NHS-Ester of PCP Acid

PCP-acid (150 mg, $4.35 \times 10^{-4}$ mole), NHS (65 mg, $5.65 \times 10^{-4}$ mole) and DCC (112 mg, $5.49 \times 10^{-4}$ mole) were placed in a 5 ml flask. The flask was connected to a vacuum for 30 minutes and then 4 ml of DMF (dried and disilled over $CaH_2$) were added under an argon atmosphere. The solution (heterogeneous) was allowed to stir at room temperature for 40 hours.

EXAMPLE V

Conjugation of PCP Acid to G6PDH

G6PDH is processed to obtain a protein concentration by UV of 2.5–3.0 mg/ml in 0.055 M Tris HCl buffer (8.2 pH). The necessary volume of enzyme solution is aliquoted into a reaction flask equipped with a stirring bar and cooled to 0°–2° C. G6P-disodium salt (20 mg/ml) and NADH (30 mg/ml) are added to the enzyme solution. The resulting mixture is stirred until a solution is obtained and carbitol (freshly distilled) is added slowly over a period of 5–10 min to a final concentration of 300 μl/ml. The pH is adjusted within a range of pH 8.5–9.0 with 1.0 N NaOH.

The activated ester (Example IV) is added at a rate of 1 to 2 μl per minute to the enzyme solution to reach a 40:1 hapten to enzyme ratio. Additional amounts of activated ester are added as deemed necessary until reaching 63–68% maximum inhibition and 17–20% deactivation.

The crude enzyme conjugate is purified by desalting through a Sephadex ® G-50 column. The conjugate is eluted with 0.055 M Tris-HCl pH 8.0 buffer with preservatives, and enzyme fractions are collected. Fractions containing enzyme activity of more than 300ΔOD units (using a 15 second delay and 30 second read time on a Gilford Spectrophotometer set at 30° C. and concentration mode) are pooled. The final enzyme parameters are then determined. The maximum inhibition does not change and should be approximately 65%, and the deactivation may increase to 30–40%.

CROSS-REACTIVITY

Referring to Table 1 below, the cross-reactivity of the PCP oxime antibodies of the present invention was checked against dextromethorphan, demerol and chlorpromazine. Four sheep were immunized with antigen according to Example II. The antisera produced at the F bleed was used in comparative assays employing the G6PDH conjugate of PCP oxime (Example III) in the competitive binding technique as described.

The following reagents were employed:

Assay buffer: 0.055 M Tris-buffer; 0.005% Thimerosol; 0.05% sodium azide; 0.5% NaCl; 0.01% Triton X-100; conc. HCl to bring pH to 8.1.

Enzyme diluent: 0.055 M Tris-HCl buffer, pH 8.1; 0.05% Thimerosol; 0.05% sodium azide; 0.9% NaCl; 1.0% RSA.

Antibody dilient: 0.055 M Tris-HCl buffer; 1.0% RSA; 0.04 M NAD; 0.066 M G6P; 0.05% sodium azide; 0.005% Thimerosol; pH adjusted to 5.0 with 5.6 N NaOH.

The enzyme reagent employs sufficient enzyme conjugate in enzyme diluent such that the maximum rate does not exceed 550 OD units. In carrying out the assay a Gilford 300 N micro-sample spectrophotometer with a Thermocuvette was employed.

The protocol of the assay is as follows: 50 μl of the sample is drawn up into a diluter-pipetter and dispensed with 250 μl of the assay buffer into a 1 ml Croan cup, followed by addition of 50 μl of the antibody reagent (antibody in antibody diluent optimized for assay), 250 μl of assay buffer, followed by 50 μl of the enzyme reagent and 250 μl of assay buffer. Immediately after the enzyme addition, the entire sample is aspirated into the flow cell. After 15 sec. a first reading is taken, followed by a second reading after a 30-sec. interval. The results are reported as the difference in absorbance $\times 2.667$.

Using a comparison level of 75 ng/ml PCP, it was found that a minimum of 50 μg/ml of dextromothorphan was required to obtan the same signal. The comparison levels for demerol and chlorpromazine were 40 μg/ml and 50 μg/ml, respectively. Thus, the reagents of the present invention displayed no significant activity with the compounds of most concern which may be present in the sera to be tested.

TABLE 1

| CROSS REACTIVITY EQUAL TO 75 ng/ml PCP | | |
|---|---|---|
| Antiserum | Drug | Equivalent Reactivity |
| BgG | Dextromethoraphan | ~65μg/ml |
|  | Chlorpramazine | >75μg/ml |
|  | Demerol | ≧40μg/ml |
| BgG | Dextramethorphan | >75μg/ml |
|  | Chlorpromazine | >75μg/ml |
|  | Demerol | >40μg/ml |
| BSA | Dextramethorphan | ~50μg/ml |
|  | Chlorpromazine | >75μg/ml |
| BSA | Dextramethorphan | ~70μg/ml |
|  | Chlorpromazine | >75μg/ml |

Table 2 summarizes cross reactivity data for a large number of drugs and PCP metabolites for the PCP oxime antibodies of the present invention in urine assays with the PCP acid conjugate of G6PDH (Example V). No significant activity was found with drugs unrelated to PCP (GROUP 1). Substantially greater activity was found for related compounds (GROUP 2), such as PCP metabolites, whose presence in urine indicates PCP use.

TABLE 2

CROSS REACTIVITY VALUES IN URINE USING OXIME ANTIBODIES AND ACID G6PDH CONJUGATE

| Cross Reactant | Levels in μg Equivalent to 75 ng/ml of PCP in Urine | |
|---|---|---|
| Dextromethoraphan | 80 | |
| Chlorpromazine | 300 | |
| Meperidine | 220 | |
| Promethazine | 350 | |
| Ketamine | >500 | |
| Imiprimine | 330 | GROUP 1[1] |
| 1-Phenylcyclohexylamine | >100 | |
| 1-[1-(2-Thienyl)-Cyclohexyl] Morpholine | 32 | |
| 1-(1-cynohexyl) piperidine[3] | >100 | |
| Morphine | >500 | |
| Cyclohexyl Metabolite | 0.38 | |
| 1-(1-Phenylcyclohexyl)-4-Hydroxypiperidine (Metabolite) | 0.38 | |
| N,N—Diethyl-1-Phenyl Cyclo-Hexylamine | 1.15 | |
| 1-(1-Phenylcyclohexyl)-Pyrolidine | 0.19 | GROUP 2[2] |
| 1-(1-Phenylcyclohexyl) Morpholine | 0.31 | |
| 1-[1-(2-Thienyl)-Cyclohexyl] Pyproleidine | 0.12 | |
| 1-[1-(2-Thienyl)-Cyclohexyl] Piperidine | 0.115 | |

[1]These compounds are unrelated to phencyclidine and it is desirable that these compounds display a low cross-reactivity, i.e., require a substantially higher level to produce an equivalent signal.
[2]These compounds are analogs, metabolites or drugs related to phencyclidine and it is desirable that these compounds react one to one with phencyclidine.
[3]Intermediate used to prepare PCP.

The compositions of the subject invention provide for reagents which provide a sensitive, accurate assay for phencyclidine, distinguishing phencyclidine from closely related metabolites which are encountered in samples. The antigenic conjugate provides for the efficient production of antibodies having high affinity and high titer for phencyclidine. The combination of the antibodies and enzyme conjugates result in an accurate rapid assay for phencyclidine in serum.

Although the foregoing invention has been described in some detail by way of illustration and example for purposes of clarity and understanding, it will be obvious that certain changes and modifications may be practiced within the scope of the claims.

What is claimed is:

1. A compound of the formula:

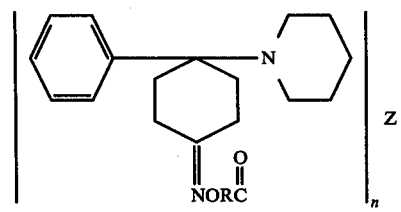

wherein:
R is a saturated aliphatic linking group of from one to six carbon atoms;
Z is hydrogen, hydroxyl, alkoxyl having from one to six carbon atoms, a group forming an activated ester capable of amine formation in an aqueous medium, or a poly(amino acid) which is antigenic or an enzyme; and
n is one when Z is other than a poly(amino acid) and otherwise is the molecular weight of Z divided by 500.

2. A compound of the formula:

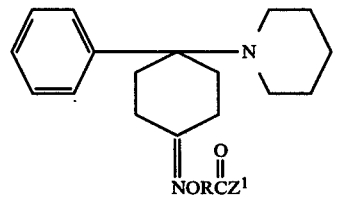

wherein:
R is a saturated aliphatic linking group of from one to six carbon atoms,
$Z^1$ is hydrogen, hydroxyl, alkoxyl of from one to six carbon atoms, or a group forming an activated ester capable of amide formation in an aqueous medium.

3. A compound of the formula:

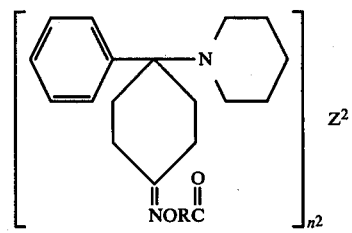

wherein:
R is a saturated aliphatic linking group of from one to six carbons;
$Z^2$ is a poly(amino acid), which is antigenic or an enzyme; and
$n^2$ is at least one and not greater than the molecular weight of $Z^2$ divided by 1,000.

4. A compound according to any of claims 1, 2 or 3, wherein R is of from one to three carbons.

5. A compound according to any of claims 1, 2 or 3, wherein R is a methylene group.

6. A compound according to claim 3, wherein n is in the range of from 2 to 500 and $Z^2$ is an antigen.

7. A compound according to claim 3, wherein n is in the range of from 2 to 20 and $Z^2$ is an enzyme.

8. A compound according to claim 7, wherein $Z^2$ is glucose-6-phosphate dehydrogenase.

9. Antibodies prepared in response to a compound according to claim 6, capable of binding to phencyclidine.

* * * * *